United States Patent
Ku

(10) Patent No.: US 11,116,801 B2
(45) Date of Patent: Sep. 14, 2021

(54) COMPOSITION CONTAINING ENDOMETRIAL DECIDUAL CELLS FOR TREATING DAMAGE TO THE ENDOMETRIUM OR ENHANCING IMPLANTATION FUNCTIONS

(71) Applicant: SEOUL NATIONAL UNIVERSITY R&DB FOUNDATION, Seoul (KR)

(72) Inventor: Seung-Yup Ku, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 315 days.

(21) Appl. No.: 16/336,626

(22) PCT Filed: Sep. 26, 2017

(86) PCT No.: PCT/KR2017/010645
§ 371 (c)(1),
(2) Date: Mar. 26, 2019

(87) PCT Pub. No.: WO2018/056795
PCT Pub. Date: Mar. 29, 2018

(65) Prior Publication Data
US 2019/0240261 A1    Aug. 8, 2019

(30) Foreign Application Priority Data
Sep. 26, 2016  (KR) .................. 10-2016-0123350

(51) Int. Cl.
| | | |
|---|---|---|
| *A61P 15/08* | (2006.01) | |
| *A61K 31/728* | (2006.01) | |
| *A61K 35/48* | (2015.01) | |
| *A61K 35/50* | (2015.01) | |
| *A61K 38/20* | (2006.01) | |

(52) U.S. Cl.
CPC ............ *A61K 35/50* (2013.01); *A61K 31/728* (2013.01); *A61K 35/48* (2013.01); *A61K 38/2093* (2013.01); *A61P 15/08* (2018.01)

(58) Field of Classification Search
CPC ........ A61K 31/728; A61K 35/48; A61P 15/08
See application file for complete search history.

(56) References Cited

FOREIGN PATENT DOCUMENTS

| KR | 10-2000-0071053 A | 11/2000 |
| KR | 10-2005-0052548 A | 6/2005 |
| WO | WO 2007/028169 A2 | 3/2007 |

OTHER PUBLICATIONS

International Search Report for PCT/KR2017/010645 dated Jan. 8, 2018 from Korean Intellectual Property Office.
Ha Zhu et al., "Endometrial stromal cells and decidualized stromal cells: Origins, transformation and functions", Gene, Aug. 26, 2014, pp. 1-14, vol. 551, No. 1.
Lijun Ding et al., "Transplantation of bone marrow mesenchymal stem cells on collagen scaffolds for the functional regeneration of injured rat uterus", Biomaterials, Mar. 27, 2014, pp. 4888-4900, vol. 35, No. 18.
Herve Dechaud, M.D. et al., "Mesothelial cell—associated hyaluronic acid promotes adhesion of endometrial cells to mesothelium", Fertility & Sterility, Nov. 2001, pp. 1012-1018, vol. 76, No. 5.
Jeremy J.G. Brown et al., "Distribution of hyaluronan in the mouse endometrium during the periimplantation period of pregnancy", Differentiation, Aug. 24, 1992, pp. 61-68, vol. 52, No. 1.

*Primary Examiner* — Daniel C Gamett
(74) *Attorney, Agent, or Firm* — Paratus Law Group, PLLC

(57) ABSTRACT

Disclosed are a pharmaceutical composition for treatment of endometrium damage, a composition for enhancing implantation ability, and a pharmaceutical composition for prevention or treatment of infertility or subfertility. The pharmaceutical composition for treatment of endometrium damage includes decidual endometrial stromal cells and hyaluronic acid, the composition for enhancing implantation ability includes decidual endometrial stromal cells and hyaluronic acid, and the pharmaceutical composition for prevention or treatment of infertility or subfertility includes decidual endometrial stromal cells and hyaluronic acid.

8 Claims, 5 Drawing Sheets

Nulliparous EMSCs
(8 weeks old)

two weeks
10nM E2+
10uM P4

In vitro decidualization

| Process | Embryo implantation rate % | Number of tested animals | Total number of embryos | Number of implanted embryos | Average number of implanted embryos |
|---|---|---|---|---|---|
| Comparative group | 54% | 5 | 50 | 27 | 5.4 |
| Damaged comparative group | 0% | 5 | 50 | 0 | 0 |
| Cell treatment group | 36% | 5 | 50 | 18 | 3.6 |
| Decidual cell and hyaluronic acid mixture treatment group | 42% | 5 | 50 | 21 | 4.2 |
| Decidual cell and LIF-added hyaluronic acid mixture treatment group | 46% | 5 | 50 | 23 | 4.6 |

COMPOSITION CONTAINING ENDOMETRIAL DECIDUAL CELLS FOR TREATING DAMAGE TO THE ENDOMETRIUM OR ENHANCING IMPLANTATION FUNCTIONS

CROSS-REFERENCE TO PRIOR APPLICATIONS

This application is a National Stage patent application of PCT International Patent Application No. PCT/KR2017/010645 (filed on Sep. 26, 2017) under 35 U.S.C. § 371, which claims priority to Korean Patent Application No. 10-2016-0123350 (filed on Sep. 26, 2016), which are all hereby incorporated by reference in their entirety.

BACKGROUND

The present disclosure relates to a composition for the treatment of endometrium damage or for enhancing implantation ability, the composition containing decidual endometrial stromal cells. More specifically, the present disclosure relates to a pharmaceutical composition for treating endometrium damage, the composition containing decidual endometrial stromal cells and hyaluronic acid, and to a method for treating endometrium damage using the pharmaceutical composition, and to a composition for enhancing implantation ability including the pharmaceutical composition, to a composition for the prevention or treatment of infertility or subfertility including the pharmaceutical composition, and to a method for the prevention or treatment of infertility or subfertility including the pharmaceutical composition.

Endometrium refers to cells defining a contour of an endometrial space and plays a key role in implantation of embryos. Endometrium secretes growth factors and cytokines to provide an embryonic implantation and development environment. Such endometrium changes in a shape and functionally according to a certain cycle via the regulation of estrogen and progesterone. Endometrial stromal cells differentiate into decidual cells in the menstrual cycle and early pregnancy. Successful differentiation into decidual cells plays a very important role in embryo implantation in mammals. During decidualization, decidualization-specific genes such as prolactin and IGF (insulin-like growth factor) are expressed. In this connection, a shape of the cell changes from an elongated shape to a round shape and to have a large cytoplasm. In vitro, the decidualization process can be induced by treating the endometrium cells with estrogens and progesterone (Ha Zhu et al., Gene, 2014, 551 (1): 1-14).

Recently, infertility/subfertility is increasing with the aging of the mother who gives birth together with the aging society. Environmental pollution due to industrial pollution and the advancement of women into society may cause the stress of women to be increasing, and the pregnancy rate is significantly lowered. Common known causes of female infertility or subfertility include ovulation disorders, transfer disorders of embryos, and implantation disorders. Among them, a reliable curing method for the infertility due to the implantation disorder has yet to be clarified.

Normal pregnancy progresses in the order of insemination, implantation and fetal development. In the implantation of the embryo, the quality of the embryo, the thickness of the endometrium and the receptivity thereof are important factors. In particular, with regard to the endometrium, when the embryo moves to the inside of the uterus and attempts implantation thereto, a first factor for the implantation is the thickness of the endometrium. The thickness of the endometrium should be at least 7 mm and is known to be 10 to 14 mm for healthy women.

The irreversible endometrium damage is caused by uterine surgery, tuberculosis infection, or endometrium infection. This causes fibrous scars in the endometrium, leading to abortion and infertility/subfertility. In particular, the damage to the endometrium due to various causes described above causes a decrease in function of the uterus, which makes it difficult to for the endometrium to maintain a normal level of the thickness. Thus, the implantation is not performed properly. When the implantation occurs, the embryo will not develop normally.

Such endometrium damage requires cell or tissue material engineering treatments. Cellular therapy of endometrium damage using collagen and bone marrow stem cells in a rodent model has been reported. However, the treatment period was reported to require more than three months (Ding L et al., Biomaterials, 2014, 35 (18): 4888-4900). Therefore, there is a continuing need to develop a method for effectively treating endometrium damage.

Furthermore, hyaluronic acid is a complex of polysaccharides and is a substance present in the body. In this complex, the polysaccharide is composed of repeats between disaccharide and β-1,4-D-glucuronic acid-β-1,3-N-acetyl-D-glucosamine. Hyaluronic acid is known as an important constituent of an intracellular support and to play an important role in maintaining the shape of cells and tissues.

SUMMARY

The present inventors have made an effort to develop ways to treat endometrium damage. We have therefore effectively treated endometrium damage by implanting a mixture between decidual endometrial stromal cells and hyaluronic acid into the damaged endometrium. Furthermore, we improved the implantation rate by implanting a mixture between decidual endometrial stromal cells and hyaluronic acid into the endometrium. In this manner, the composition containing the decidual endometrial stromal cell and hyaluronic acid could be useful for the treatment of endometrium damage and the enhancement of implantation ability.

One purpose of the present disclosure is to provide a pharmaceutical composition for treatment of endometrium damage, the composition containing decidual endometrial stromal cells and hyaluronic acid.

Another purpose of the present disclosure is to provide a treatment method of endometrium damage, including a step of administering the composition to the uterus-damaged individual.

Another purpose of the present disclosure is to provide a composition for enhancing implantation ability, the composition containing decidual endometrial stromal cells and hyaluronic acid.

Another purpose of the present disclosure is to provide a pharmaceutical composition for the prevention or treatment of infertility or subfertility, the composition containing decidual endometrial stromal cells and hyaluronic acid.

Another purpose of the present disclosure is to provide a method of prevention or treatment of infertility or subfertility, the method including administering the pharmaceutical composition for the prevention or treatment of the infertility or subfertility to an individual having infertility or subfertility due to decreased function of the uterus or endometrium damage.

According to the present disclosure, the composition containing decidual endometrial stromal cells and hyaluronic acid is administered to the entity having the damaged uterus, to recover the damaged uterus and further improve the implantation rate. Thus, the composition may be useful as a composition for treatment of endometrium damage, a composition for enhancing implantability, and a composition for the prevention or treatment of infertility or subfertility.

DETAILED DESCRIPTION

Figure 1:
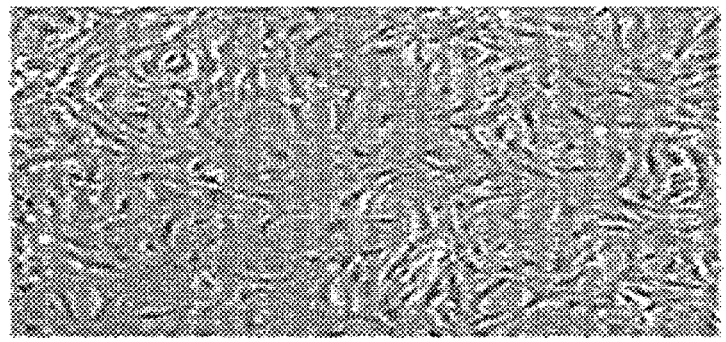
FIG. 1 shows a process of decidualizing isolated endometrium cells.
Figure 1:
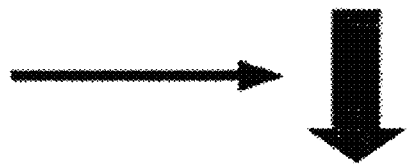
Figure 1:
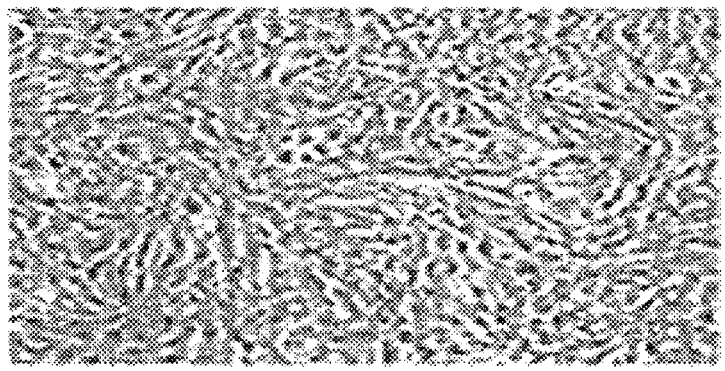

According to the present disclosure, when a mixture of decidual endometrial stromal cells and hyaluronic acid was implanted into a uterus-damaged mouse, the damaged uterus was recovered and the pregnancy ability or implantation ability was improved. Thus, the present disclosure is directed to a composition for the treatment of endometrium damage or for enhancing implantation ability, the composition containing decidual endometrial stromal cells. More specifically, the present disclosure relates to a pharmaceutical composition for treating endometrium damage, the composition containing decidual endometrial stromal cells and hyaluronic acid, and to a method for treating endometrium damage using the pharmaceutical composition, and to a composition for enhancing implantation ability including the pharmaceutical composition, to a composition for the prevention or treatment of infertility or subfertility including the pharmaceutical composition, and to a method for the prevention or treatment of infertility or subfertility including the pharmaceutical composition.

The present disclosure will be described in detail as follows. Each description and embodiment as disclosed in the present disclosure may be applied to another description and embodiment. That is, all combinations of various elements disclosed in the present disclosure fall within the category of the present disclosure. Further, the following description does not limit the scope of the present disclosure.

One aspect according to the present disclosure to achieve this purpose is directed to the pharmaceutical composition for the treatment of endometrium damage containing decidual endometrial stromal cells and hyaluronic acid.

As used herein, the term "damage of endometrium" refers to the destruction of normal integrity of all or part of the endometrium tissue due to causes such as uterine surgery, tuberculosis infection, physical damage or endometrium infection. The damage of endometrium is intended to include wounds, lesions, necrosis and ulcers. Damage to the endometrium can lead to infertility/subfertility, because the embryo cannot be implanted due to the damage or the damage can cause abnormal embryonic development.

As used herein, endometrium cells represent endometrial stromal cells. The two terms are used interchangeably.

As used herein, the decidualization of the endometrial stromal cell refers to a modification caused by progesterone as properties of the uterus of a pregnant individual. Thus, the term "decidual endometrial stromal cells" may refer to cells that exhibit the same/similar properties as those of the endometrium cells modified by progesterone in vivo. Specifically, the decidual endometrial stromal cell may be obtained by treating endometrium cells with estrogens and progesterone for 5 to 15 days. Alternatively, when the endometrium cells were differentiated into decidual endometrial stromal cells, prolactin is secreted and/or IGF-1 (insulin like growth factor-1) gene is expressed. However, the present disclosure is not limited thereto.

The decidual endometrial stromal cell may be produced as follows: In vitro, the differentiation of stem cells (such as embryonic stem cells, pluripotent stem cells such as inducible pluripotent stem cells or multipotent stem cells such as mesenchymal stem cells) into endometrium cells is induced and the differentiated cells are decidualized. Alternatively, the decidual endometrial stromal cell may be produced by decidualizing isolated endometrium cells.

The pharmaceutical composition for treatment of endometrium damage according to the present disclosure is achieved by mixing the decidual endometrial stromal cell and hyaluronic acid. The composition can be implanted into a damaged area of the endometrium to treat endometrium damage. This treatment effect may be caused by the fact that the implanted decidual endometrial stromal cell is merged into the damaged tissue and then is divided. Alternatively, the hormone and/or cytokine secreted from the implanted cells may naturally promote the differentiation/division of cells present in the entity to cause the above effect. The present disclosure is not limited thereto. In particular, this effect may be significantly increased by implanting a mixture of hyaluronic acid and the decidual endometrial stromal cell, as compared to a implantation of only the decidual endometrial stromal cells. Furthermore, the damaged endometrium may be restored, thereby increasing the implantation rate of the embryo. Thus, the composition may be used for the treatment of infertility or subfertility due to endometrium damage.

Specifically, the composition may be obtained by mixing 50 to 200 μl of hyaluronic acid per $1 \times 10^5$ to $1 \times 10^6$ decidual endometrial stromal cells. The hyaluronic acid may be present in a concentration of 5 mg/ml to 15 mg/ml, but is not limited thereto.

Further, the composition may further contain a leukemia inhibitory factor (LIF). The LIF may be mixed into the composition at a concentration of $10^2$ to $10^4$ unit/ml. The implantation rate can be further improved when the composition has the LIF. Furthermore, growth factors or cytokines, such as epidermal growth factor (EGF), etc., that can further improve the implantation rate may be further contained in the composition.

Figure 2:
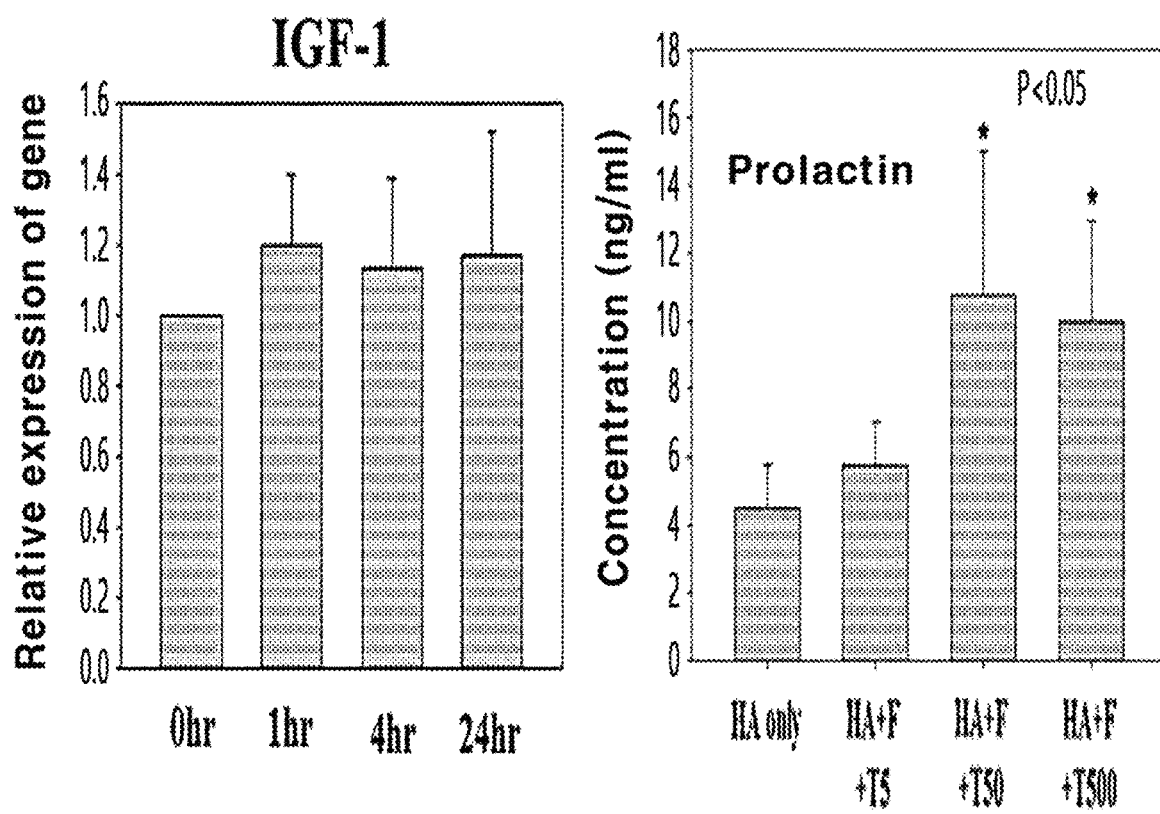
FIG. 2 shows an expression level of insulin like growth factor-1 (IGF-1) gene and a secretion level of prolactin for differentiated cells.
Figure 4:
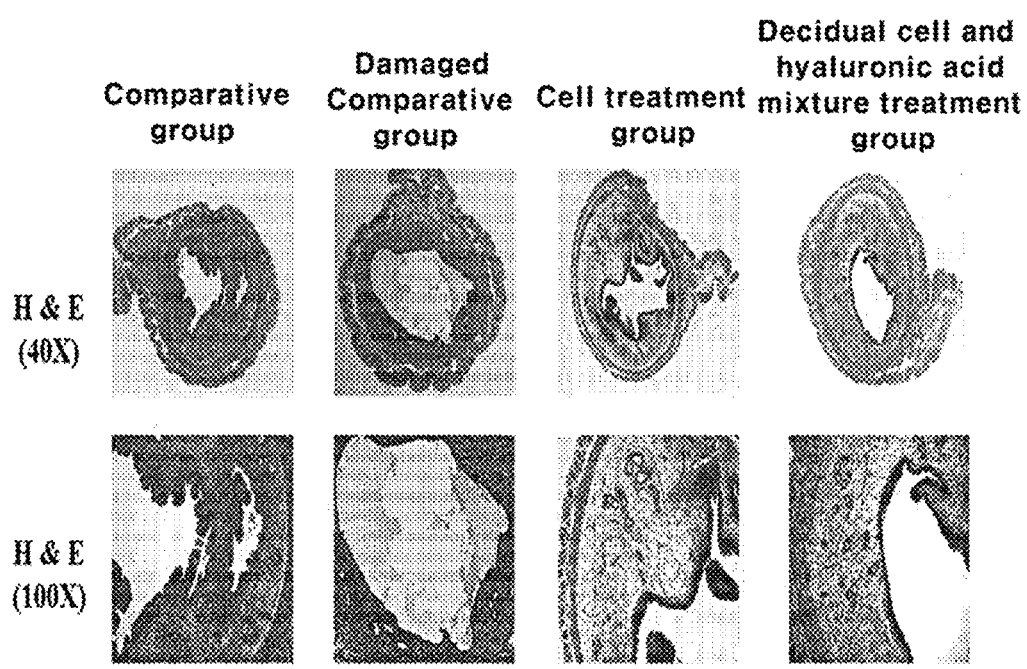
FIG. 4 is a photograph of a stained tissue of an uterine damaged mouse after a decidual endometrial stromal cell and hyaluronic acid are transplanted to the uterine damaged mouse.
Figure 5:
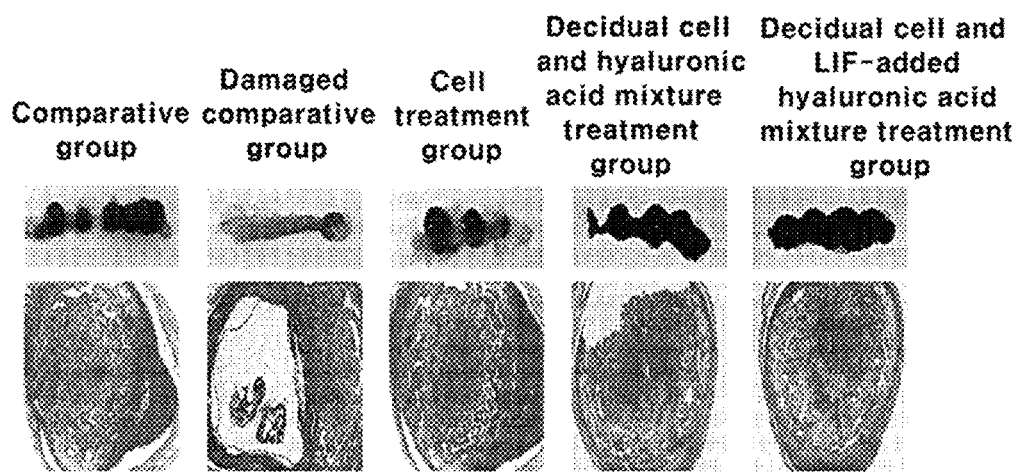
FIG. 5 shows a result of an implantation rate and embryo development after transplantation of decidual endometrial stromal cells and hyaluronic acid (or additionally LIF) to the uterine damaged mouse is performed and then the mouse is pregnant.

In one specific embodiment according to the present disclosure, the endometrium cells were treated with estradiol and progesterone to induce decidualization thereof to produce decidual endometrial stromal cells (FIG. 1 and FIG. 2). The produced decidual endometrial stromal cells were then mixed with hyaluronic acid. Then, the mixture was implanted into the damaged portion of the uterus-damaged mouse. As a result, the uterine tissue was remarkably recovered as compared with a control group as injected with only the endometrium cells (FIG. 4). The implantation rate was improved (FIG. 5). Furthermore, these effects were further improved when further mixing LIF with the composition (FIG. 5). Therefore, the pharmaceutical composition according to the present disclosure has an excellent effect when used as a treatment for endometrium damage. Thus, the composition is expected to be useful for infertility or subfertility treatment due to endometrium damage or loss of uterine function.

The composition for the treatment according to the present disclosure is intended for administration thereof to patients with endometrium damage. Such compositions may be produced in the form of formulations well known in the art, such as injections. The composition may be implanted directly into the surgically damaged endometrium. The composition may be administered intravenously and then moved to the damaged site. The composition for the treatment according to the present disclosure may contain an additional immunosuppressive agent to prevent the immune rejection at the time of implantation. Further, the composition may be carried in a pharmaceutically acceptable carrier. The amount of administration of the composition for treatment according to the present disclosure may vary depending on the severity of the patient, the administration route, the administration method, the number of administrations, the duration of treatment, the age of the patient, etc. This amount may be readily determined by those skilled in the art according to factors well known in the medical arts.

Another aspect according to the present disclosure is directed to the treatment method of endometrium damage, the method including the step of administering the composition to the uterine damaged entity.

The composition and endometrium damage are as described above.

Administration of the composition containing the decidual endometrial stromal cell and hyaluronic acid according to the present disclosure is applicable to any animal. Animals may include human and primate as well as livestock such as cows, pigs, sheep, horses, dogs, mice, rats and cats.

As used herein, the term "administration" means introducing the composition according to the present disclosure to an endometrium damaged entity using any appropriate method. The administration includes the implantation of the composition. The composition according to the present disclosure may be administered through various routes as long as the composition can reach a target tissue. Preferably, the composition may be administered to the damaged uterine tissue.

Another aspect of the present disclosure is directed to a composition for enhancing implantation ability, the composition containing decidual endometrial stromal cells and hyaluronic acid.

Further, the composition may be used to promote implantation of an inseminated embryo to promote pregnancy.

The decidual endometrial stromal cell and hyaluronic acid have been described above.

As used herein, the term "enhancing implantation ability" means that a process may be promoted in which the inseminated embryo created by the combination of the ovum and the sperm is implanted into the uterus and then develops into the fetus. This term may specifically mean increasing the probability of implantation of the inseminated embryo into the endometrium, or promoting the process of implantation of the inseminated embryo into the endometrium, thereby promoting the pregnancy probability.

As used herein, the term "inseminated embryo" refers to an initial stage of development ranging from a time when the zygote in which the ovum and sperm are combined begins to divide more than once to a time before the zygote becomes a complete entity. Specifically, this inseminated embryo at the initial stage of development may be an in vitro inseminated embryo, but is not limited thereto. Further, as used herein, the term "implantation" refers to a state in which an inseminated embryo adheres to the lining of the uterus such that the fetus receives oxygen and nutrients from the mother.

In one specific embodiment according to the present disclosure, the endometrium cells were treated with estradiol and progesterone to induce decidualization thereof to produce decidual endometrial stromal cells (FIG. 1 and FIG. 2). The produced decidual endometrial stromal cells were then mixed with hyaluronic acid. Then, the mixture was implanted into the damaged portion of the uterus-damaged mouse. As a result, the uterine tissue was remarkably recovered as compared with a control group as injected with only the endometrium cells (FIG. 4). The implantation rate was improved (FIG. 5). Furthermore, these effects were further improved when further mixing LIF with the composition (FIG. 5). Therefore, the pharmaceutical composition according to the present disclosure has an excellent effect when used as a treatment for endometrium damage. Therefore, the composition according to the present disclosure is expected to improve the implantation ability or to promote pregnancy by restoring the uterine function via treating endometrium damage.

The composition may be applied to a food composition for promoting implantation ability for promoting implantation of an inseminated embryo, an animal-feed composition for enhancing implantation ability, or a quasi-drug composition for enhancing implantation ability.

The food composition may include a functional food.

Since a safety of the decidual endometrial stromal cell and hyaluronic acid has proven, they may be produced in a form of foods that may be consumed constantly and promote the implantation ability or promote pregnancy.

The functional food is the same term as FoSHU (food for special health use). The functional food means foods with high medical efficacy that have been processed so that the bio-control function can be efficiently demonstrated therefrom in addition to nutritional supplementation. To obtain a beneficial effect in promoting implantation ability or promoting pregnancy, the food may be produced in various forms such as tablets, capsules, powders, granules, liquids, pills, and the like.

The food composition according to the present disclosure may further include a pharmaceutically acceptable carrier.

There is no particular restriction on a type of food that may contain the composition containing decidual endometrial stromal cells and hyaluronic acid according to the present disclosure. For example, the food may be various beverages, gums, tea, vitamin complexes, and health supplement foods. The food composition may additionally contain other ingredients that do not interfere with the effect of promoting implantation or promoting pregnancy. A type of such a component is not particularly limited. For example, various herbal medicine extracts, food-acceptable additives or natural carbohydrates may be contained as the additional ingredient, as in ordinary foods.

The food-aid additive is added for production of a functional food of each formulation and is appropriately selected by those skilled in the art. For example, food-aid additives may include various nutrients, vitamins, minerals (electrolytes), various flavoring agents such as synthetic flavors and natural flavors, colorants and fillers, pectic acid and its salts, alginic acid and its salts, organic acids, protective colloid thickening agents, pH adjusting agents, stabilizers, preservatives, glycerin, alcohols, and carbonating agents used in carbonated drinks. The food-aid additive is not limited to the above examples.

The health functional food according to the present disclosure may be produced by a method commonly used in the art. In the production, raw materials and components that are conventionally added in the art may be added to the food. Thus, there is an advantage that the food is used as a raw material unlike a general medicine and thus there are no side effects that may otherwise occur when a medicine is taken for a long time. Further, a portability of the food may be excellent.

The animal-feed composition may contain an animal-feed additive. The animal-feed additive according to the present disclosure may belong to an auxiliary animal-feed under an animal-feed management regulation.

As used herein, the term "animal-feed" may mean any natural or artificial diet, meal, or ingredients of the meal which the animals may eat, ingest and digest.

A type of the animal-feed is not particularly limited. Animal-feeds commonly used in the art may be employed. Non-limiting examples of the animal-feed may include vegetable animal-feeds such as cereal crops, root crops, food processing by-products, algae, fibers, pharmaceuticals by-products, oils, starch, vegetable residues; and animal-feeds of animal origin such as proteins, inorganics, oils, minerals, monocellular proteins, zooplankton or foods of animal origin. These may be used alone or in combination of two or more.

As used herein, the term "quasi-drug" may be defined as articles made from fiber, rubber, or similar materials used in humans or animals for the purpose of curing, alleviating, treating, or preventing diseases; articles, other than instruments, machines or the like, which have a mild action on or have no direct influence on the human body; and, articles, falling within the range of agents used to sterilize, kill insects and for similar purposes. All of the articles exclude those intended at the same time to be prescribed to diagnose, cure, alleviate, treat or prevent diseases in humans or animals, and for pharmaceutically affecting the structure and function of humans or animals. In addition, the quasi-drug may include a skin external preparation and a personal hygiene product. Examples of the quasi-drug to which the composition of the present disclosure may be applied include, but are not limited to, disinfectants, shower foams, mouthwash, wet tissues, detergent soap, handwashing materials, humidifier fillers, masks, ointments, and a filter coating.

When the composition according to the present disclosure is used as a quasi-drug additive, the composition may be added as is or in combination with other quasi-drugs or quasi-drug components. The quasi-drug may be suitably used according to conventional methods. An amount of the active ingredient to be mixed may be suitably determined according to the purpose of use.

Another aspect according to the present disclosure is directed to a pharmaceutical composition for the prevention or treatment of infertility or subfertility, the composition containing decidual endometrial stromal cells and hyaluronic acid.

The decidual endometrial stromal cell and hyaluronic acid have been described above.

As used herein, the term "infertility or subfertility" means that a couple without contraception cannot reach the pregnancy within one year despite their normal sexual intercourse. The infertility or subfertility may refer to non-implantation of ovum or female infertility of uterine origin but may not be limited thereto. More specifically, the term may refer to an infertility or subfertility due to endometrium damage or uterine dysfunction.

The composition may be used as a food composition, an animal-feed composition, or a quasi-drug composition for preventing or treatment infertility or subfertility as well as the pharmaceutical composition for preventing or treating infertility or subfertility.

In one specific embodiment according to the present disclosure, the endometrium cells were treated with estradiol and progesterone to induce decidualization thereof to produce decidual endometrial stromal cells (FIG. 1 and FIG. 2). The produced decidual endometrial stromal cells were then mixed with hyaluronic acid. Then, the mixture was implanted into the damaged portion of the uterus-damaged mouse. As a result, the uterine tissue was remarkably recovered as compared with a control group as injected with only the endometrium cells (FIG. 4). The implantation rate was improved (FIG. 5). Therefore, the composition according to the present disclosure may treat the damage of the endometrium to restore the function of the uterus. Thus, the composition according to the present disclosure may be expected to be used to treat the infertility or subfertility resulting from the damaged endometrium or the uterus function deterioration.

Another aspect according to the present disclosure is directed to a method for preventing or treating infertility or subfertility, the method including administering the pharmaceutical composition for the prevention or treatment of the infertility or subfertility to an entity having infertility or subfertility caused by endometrium damage or loss of uterine function.

The pharmaceutical composition, endometrium damage, and infertility or subfertility are as described above.

Administration of the composition containing the decidual endometrial stromal cell and hyaluronic acid according to the present disclosure is applicable to any animal. Animals may include human and primate as well as livestock such as cows, pigs, sheep, horses, dogs, mice, rats and cats.

As used herein, the term "administration" refers to introducing, in any appropriate method, the composition in accordance with the present disclosure to an entity having infertility or subfertility, specifically, an entity with infertility or subfertility as caused by damage to the endometrium or loss of function of the uterus. The administration may include implantation of the composition. The composition according to the present disclosure may be administered through various routes as long as the composition can reach a target tissue. The composition may be administered to damaged tissues, and preferably to damaged tissues, or tissues having the uterine function deterioration.

EXAMPLES

The present disclosure is described in more detail using the Present Examples below. However, these Present Examples are meant to illustrate the present disclosure and the scope of the present disclosure is not limited to these Present Examples.

Present Example 1. Production of Decidual Endometrial Stromal Cell

Endometrial stromal cells were obtained by the following procedure. After taking uterus of an 8-week-old mouse, the uterus was extracted with forceps and scissors and was cut into a piece of a size of about 5 mm. The small piece of uterus was placed in a 1 mg/ml collagenase type I solution, and was reacted in a constant temperature water bath at 37 degrees C. for 2 hours. After the 2 hours, the solution was neutralized by adding the same amount of culture solution (DMEM/F12+10% FBS) as the collagenase, and then filtered with a nylon mesh of 70 µm size to separate only the endometrium cell in a form of a single cell. The endometrium cell obtained by the above procedure was cultured in a culture solution (DMEM/F12+10% FBS) for 2 weeks.

To decidualize the cultured endometrium cells, 10 nM estradiol and 10 µM progesterone were added to the culture solution, to induce decidualization for approximately 14 days (FIG. 1). As may be seen in FIG. 1, the decidualization resulted in a change of the shape of the cell from the elongated shape to a round shape and to have a large cytoplasm.

Further, in order to confirm the induction of the endometrium cells into decidual endometrial stromal cells, whether secretion of prolactin secreted when the endometrium cells were differentiated into decidual endometrial stromal cells and expression of IGF-1 (insulin like growth factor-1) gene when the endometrium cells were differentiated into decidual endometrial stromal cells occur was checked. It was additionally checked whether the differentiated cells had characteristics of the decidualized cells.

Specifically, the presence or absence of the expression and the expression level of IGF-1 (insulin like growth factor-1) gene as expressed from the decidualized endometrium were analyzed using real-time quantitative real-time polymerase chain reaction. Further, to determine the presence or absence of the secretion of prolactin and the secretion level thereof, the culture medium for decidualized endometrium was collected and the prolactin concentration in the culture medium was measured.

As a result, it was confirmed that when the decidualization was induced by adding the estradiol and progesterone to the culture medium, expression level of IGF-1 and prolactin secretion level were increased. This indicates that the cells were induced to be decidualized (FIG. 2). The expression level of IGF-1 based on the elapsing time after the decidualization was not statistically significant for 1 to 24 hours after induction of the decidualization. The level of secretion of prolactin was affected by the thrombin addition amount. The prolactin secretion level was statistically significantly increased for a group to which the thrombin was added at a concentration of 50 µg/ml or greater (F: fibrin, T: thrombin).

Present Example 2. Production of a Mixture of Decidual Endometrial Stromal Cell and Hyaluronic Acid The decidual endometrial stromal cell produced in Present Example 1 was mixed with hyaluronic acid which is innocuous and biodegradable in the body. Then, a treatment effect of the mixture on endometrium damage was checked.

Specifically, $1 \times 10^6$ endometrium cells as decidualized for 14 days were mixed with 100 µl of hyaluronic acid at a concentration of 10 mg/ml. The mixture was cultured in a culture medium DMEM supplemented with 10% FBS for 24 hours. Then, the cultured mixture was evaluated by scanning electron microscope (SEM).

Figure 3:
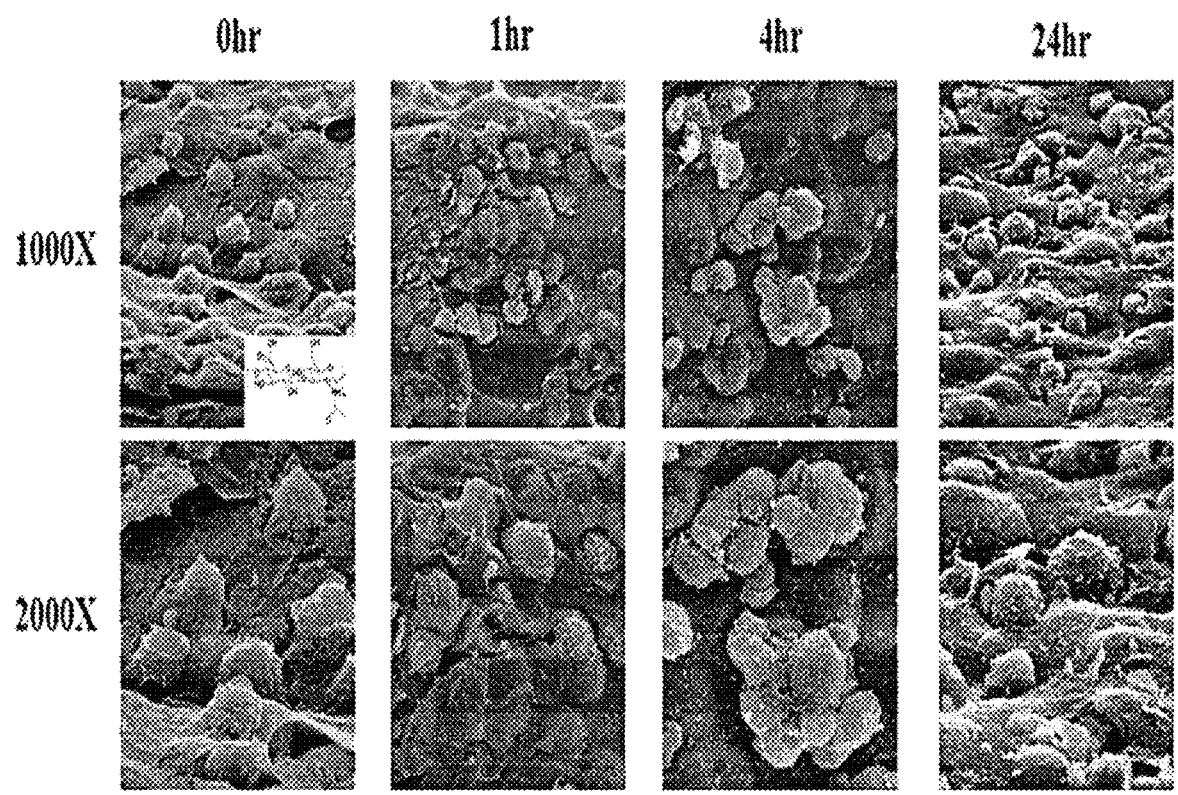
FIG. 3 is a photograph of a cultivated mixture of decidual endometrial stromal cells and hyaluronic acid.

As a result, as the time of culturing the mixture between hyaluronic acid and decidual endometrial stromal cells lapses, a cell distribution on a microstructure with well-developed cross-linking was observed (FIG. 3).

Present Example 3. Evaluation of In Vitro Recovery of Damaged Uterine Due to Mixture of Decidual Endometrial Stromal Cell and Hyaluronic Acid The uterine damaged model was prepared by injecting 50% ethanol (EtOH) into the uterus of 8-week-old female mouse (C57/BL6). Two weeks after the ethanol injection, the mixture between the decidual endometrial stromal cells and hyaluronic acid was injected into the uterus of the uterine damaged mouse. After 2 weeks, a degree at which the damaged uterine was recovered was evaluated. Normal mice, untreated uterine damaged mice, and uterine damaged mice injected with decidual cells alone were used as controls. The uterine tissue was checked via tissue staining.

As a result, the endometrium was completely damaged in the uterine damaged model mice. It was found from FIG. 4 that the uterine tissue was significantly recovered in a group injected with the mixture between decidual endometrial stromal cells and hyaluronic acid, compared with the untreated control and the control injected only with the decidual cells.

Present Example 4. Assessment of Fertility by Mixture Between Decidual Endometrial Stromal Cell and Hyaluronic Acid Next, we evaluated the fertility by the mixture between decidual endometrial stromal cell and hyaluronic acid according to the present disclosure. A mixture containing decidual endometrial stromal cells, hyaluronic acid, and Leukemia inhibitory factor (LIF) was added to the experimental group of the above Present Example 3. The effect thereof was evaluated. The LIF was added to the mixture at a concentration of $10^3$ unit/ml. Then, endometrium damage was induced in the same manner as in Present Example 3. After each treatment using the mixture, the mouse becomes pregnant. In order to induce the pregnancy, 10 blastocysts collected from female mice of the same species were injected into the uterus of the above-mentioned mouse, and then a male mouse whose reproductive ability was removed was brought to the above-mentioned female mouse. Thus, pseudocyesis was induced. The presence or absence of pregnancy was checked at 8 am via a plug check. Nine days after the pregnancy, Evans blue staining solution was prepared at a concentration of 5 mg/ml and injected into a tail vein of the pregnant female mouse at a dose of 100 µl. 15 minutes after the injection, the uterus was removed and the number of implanted embryos was checked. In order to determine the normal implantation and development of the implanted embryos, we determined the presence or absence of abnormalities via the tissue staining.

As a result, for a first group subjected to the treatment with the mixture between the decidual endometrial stromal cells and hyaluronic acid and a second group subjected to the treatment with the mixture between the decidual endometrial stromal cells, hyaluronic acid and LIF, implantation and development of the pregnant embryos as similar to those of the normal mice were observed (FIG. 5). The first group subjected to the treatment with the mixture between the decidual endometrial stromal cells and hyaluronic acid has the implantation rate of 42%. The second group subjected to the treatment with the mixture between the decidual endometrial stromal cells, hyaluronic acid and LIF has the implantation rate of 46%. Thus, the implantation rates of the embryos for the first and second groups were slightly lower than that of the normal mouse, but were significantly higher than that of the damaged group as the controls (whose implantation rate is 0%), and much higher than that of the control group as treated with the decidual endometrial stromal cells alone (whose implantation rate is 36%) (See FIG. 5).

In conclusion, the composition containing the mixture of decidual endometrial stromal cells and hyaluronic acid (or the mixture further containing LIF) according to the present disclosure functionally recovers the damaged endometrium to have a fertility level close to a normal fertility level, thus to make pregnancy possible.

Therefore, the composition containing the decidual endometrial stromal cells and hyaluronic acid according to the present disclosure may be used for treating the endometrium damage. Further, the composition containing the decidual endometrial stromal cells and hyaluronic acid according to the present disclosure may be used to promote the embryo implantation to improve the implantation ability to promote pregnancy by treating the endometrium damage to restore the uterine function. Thus, the composition may be very useful for promoting the implantation of an in vitro inseminated embryo. Further, it may be seen that the composition may be used to treat endometrium damage to prevent or treat infertility or subfertility due to uterine dysfunction or endometrium damage.

From the foregoing description, one of ordinary skill in the art to which the present disclosure belongs may understand that the present disclosure may be embodied in other specific forms without departing from the spirit or essential characteristics thereof. In this regard, it should be understood that the embodiments as described above are illustrative in all aspects and not restrictive. The scope of the present disclosure is to be construed such that all changes or modifications derived from the meaning and scope of the appended claims and their equivalents subsequent to the foregoing descriptions are included in the scope of the present disclosure.

What is claimed is:

1. A pharmaceutical composition for treatment of endometrium damage, the composition containing decidual endometrial stromal cells and hyaluronic acid.

2. The pharmaceutical composition of claim 1, wherein the decidual endometrial stromal cell secretes prolactin or expresses insulin like growth factor-1 (IGF-1).

3. The pharmaceutical composition of claim 1, wherein in the composition, 50 µl to 200 µl of the hyaluronic acid is contained per $1 \times 10^5$ to $1 \times 10^6$ decidual endometrial stromal cells.

4. The pharmaceutical composition of claim 3, wherein the hyaluronic acid has a concentration of 5 mg/ml to 15 mg/ml.

5. The pharmaceutical composition of claim 1, wherein the composition further contains a leukemia inhibitory factor (LIF).

6. The pharmaceutical composition of claim 5, wherein a content of the LIF is in a range from $10^2$ unit/ml to $10^4$ unit/ml.

7. A method for treating endometrium damage, the method comprising administering the composition of claim 1 to a uterine-damaged entity.

8. A method for prevention or treatment of infertility or subfertility, the method including administering a pharmaceutical composition containing decidual endometrial stromal cells and hyaluronic acid to an entity having infertility or subfertility resulting from endometrium damage or uterine function deterioration.

* * * * *